US011707635B2

(12) United States Patent
Zheng et al.

(10) Patent No.: US 11,707,635 B2
(45) Date of Patent: Jul. 25, 2023

(54) CONSCIOUS ANIMAL ULTRASONIC NEURAL REGULATION DEVICE

(71) Applicant: SHENZHEN INSTITUTES OF ADVANCED TECHNOLOGY CHINESE ACADEMY OF SCIENCES, Shenzhen (CN)

(72) Inventors: Hairong Zheng, Shenzhen (CN); Hui Zhou, Shenzhen (CN); Lili Niu, Shenzhen (CN); Ruibiao Guo, Shenzhen (CN); Long Meng, Shenzhen (CN); Yongchuan Li, Shenzhen (CN); Min Su, Shenzhen (CN); Jiqing Huang, Shenzhen (CN); Ming Qian, Shenzhen (CN)

(73) Assignee: SHENZHEN INSTITUTES OF ADVANCED TECHNOLOGY CHINESE ACADEMY OF SCIENCES, Shenzhen (CN)

( * ) Notice: Subject to any disclaimer, the term of this patent is extended or adjusted under 35 U.S.C. 154(b) by 671 days.

(21) Appl. No.: 16/492,405

(22) PCT Filed: Apr. 21, 2017

(86) PCT No.: PCT/CN2017/081381
§ 371 (c)(1),
(2) Date: Sep. 9, 2019

(87) PCT Pub. No.: WO2018/161413
PCT Pub. Date: Sep. 13, 2018

(65) Prior Publication Data
US 2020/0038692 A1 Feb. 6, 2020

(30) Foreign Application Priority Data
Mar. 9, 2017 (CN) .......................... 201710138442.6

(51) Int. Cl.
A61N 7/00 (2006.01)
B06B 1/02 (2006.01)
(Continued)

(52) U.S. Cl.
CPC .............. A61N 7/00 (2013.01); B06B 1/0215 (2013.01); B06B 1/067 (2013.01); A01K 29/005 (2013.01);
(Continued)

(58) Field of Classification Search
CPC .............. A61N 7/00; A61N 2007/0026; A61N 2007/0021; A61N 2007/0065;
(Continued)

(56) References Cited

U.S. PATENT DOCUMENTS

2012/0289869 A1* 11/2012 Tyler ...................... A61B 5/245
601/2
2013/0281890 A1 10/2013 Mishelevich
(Continued)

FOREIGN PATENT DOCUMENTS

CN 101698121 A 4/2010
CN 102232856 A 11/2011
(Continued)

OTHER PUBLICATIONS

Supplemental European Search Report, p. 1-9, dated Nov. 16, 2020.
(Continued)

Primary Examiner — Joseph M Santos Rodriguez
Assistant Examiner — Kaitlyn E Sebastian
(74) Attorney, Agent, or Firm — George McGuire

(57) ABSTRACT

Provided is a conscious animal ultrasonic neural regulation device, including a pulse signal generation module, a transducer module and a fixing module. The pulse signal generation module is configured to generate a pulse signal with high energy. The ultrasonic transducer module is configured (Continued)

to convert the pulse signal into an ultrasound. The fixing module includes an upper fixing module and a lower fixing module. The upper fixing module is configured to fix the ultrasonic transducer module, and the lower fixing module is configured to be fixed on an animal neural regulation target point. The upper fixing module and the lower fixing module are connected by a connecting component. The conscious animal neural regulation device of the present disclosure can perform accurate ultrasonic stimulation on a cerebral cortex and subcortex of the animal, thereby exploring and verifying the stimulation effect of the ultrasound on the animal, which is easy in operation and convenient in use.

7 Claims, 2 Drawing Sheets

(51) Int. Cl.
  *B06B 1/06* (2006.01)
  *A01K 29/00* (2006.01)
(52) U.S. Cl.
  CPC ... *A61N 2007/0026* (2013.01); *B06B 2201/76* (2013.01)
(58) Field of Classification Search
  CPC ... B06B 1/0215; B06B 1/067; B06B 2201/76; A01K 29/005; A61B 2017/00154
  See application file for complete search history.

(56) References Cited

U.S. PATENT DOCUMENTS

| | | | |
|---|---|---|---|
| 2015/0099978 A1* | 4/2015 | Davidsen | A61B 8/4444 600/459 |
| 2015/0112233 A1* | 4/2015 | Towe | A61N 1/0504 601/2 |
| 2016/0038770 A1* | 2/2016 | Tyler | A61N 7/02 601/2 |

FOREIGN PATENT DOCUMENTS

| | | |
|---|---|---|
| CN | 103028202 A | 4/2013 |
| CN | 104826243 A | 8/2015 |
| CN | 105344023 A | 2/2016 |
| CN | 105944245 A | 9/2016 |
| WO | 2015176001 A1 | 11/2015 |

OTHER PUBLICATIONS

International Search Report and Written Opinion for PCT/ISA/210 and PCT/ISA/237, International Application No. PCT/CN/2017/081381, pp. 1-5, International Filing Date Apr. 21, 2017, dated Nov. 8, 2017.

* cited by examiner

CONSCIOUS ANIMAL ULTRASONIC NEURAL REGULATION DEVICE

CROSS-REFERENCES TO RELATED APPLICATIONS

This application is a national stage application under 35 U.S.C. 371 based on international patent application PCT/CN2017/081381 filed on Apr. 21, 2017, which claims priority to Chinese Patent Application No. 201710138442.6 filed on Mar. 9, 2017, disclosures of both of which are incorporated herein by reference in their entireties.

TECHNICAL FIELD

The present disclosure relates to the field of medical instruments, particularly, to a conscious animal ultrasonic neural regulation device.

BACKGROUND

With the gradual increasing number of patients with brain diseases such as depression, Parkinson and epilepsy, the treatment of the brain functional diseases has gradually become the focus of the modern medical research. The key to studying the functional diseases is to determine the cortex in which the lesion is located and the nerve conduction pathway of the deep nucleus. The ultrasonic stimulation increasingly causes attention due to the safety, the non-invasiveness and the effectiveness of the ultrasonic stimulation. Many laboratories in the world are currently conducting research on the ultrasonic animal stimulating neural system.

The focal field of the focused ultrasonic radiation sound field is an oblong shape, which make the focused ultrasonic radiation sound field easier to perform the stimulation with high anatomical accuracy on the neural system. A conscious animal ultrasonic neural stimulation system is provided, to eliminate the influence of the anesthetic drugs on the nervous activity of animals and achieve the neural regulation of the conscious animal.

SUMMARY

An object of the present disclosure is to provide a conscious animal ultrasonic neural regulation device, which can perform accurate ultrasonic stimulation and regulation on the conscious normal animal and model animal (Parkinson, epilepsy, etc.) in a conscious state, and explore and verify the function of the ultrasound on the neural regulation in condition that the animal is in the conscious state.

In order to achieve the above object, provided is a conscious animal ultrasonic neural regulation device, including a pulse signal generation module, a transducer module and a fixing module. The pulse signal generation module is configured to generate a pulse signal with high energy. The ultrasonic transducer module is configured to convert the pulse signal into an ultrasound. The fixing module includes an upper fixing module and a lower fixing module. The upper fixing module is configured to fix the ultrasonic transducer module, and the lower fixing module is configured to be fixed on an animal neural regulation target point. The upper fixing module and the lower fixing module are connected by a connecting component.

In one embodiment, the pulse signal generation module includes: an independent two-channel signal generator, configured to generate a neural regulation pulse waveform; a power amplifier, configured to increase an energy of the regulation pulse waveform; and an impedance matching circuit, configured to perform personalization design based on an actual measured impedance value of a piezoelectric array element, to realize impedance matching.

In one embodiment, the pulse signal generation module further includes an oscilloscope connected with the independent two-channel signal generator and configured to observe an output waveform.

In one embodiment, the two-channel signal generator has a fundamental frequency at least in a range of 0.1 MHz to 5 MHz, is configured to independently generate a sinusoidal signal and a square wave signal, and has a TTL (Transistor-Transistor Logic) gate trigger output function.

In one embodiment, the power amplifier has a frequency band in a range of 0.1 MHz to 5 MHz, and a power range of 50 W to 150 W.

In one embodiment, the ultrasonic transducer module includes a leading wire, the piezoelectric array element and a backing. The piezoelectric array element is connected to the leading wire, and the leading wire is connected to the impedance matching circuit of the pulse signal generation module. The backing is made of an epoxy resin material, and provided with a water inlet and an air outlet. The water inlet is configured to inject deionized water.

In one embodiment, the piezoelectric array element is composed of a single array element, has an arc shaped structure capable of reaching a neutral regulation depth, and is configured to focus the ultrasound generated by the piezoelectric array element on an animal brain target point.

In one embodiment, a piezoelectric material of the piezoelectric array element includes a piezoelectric ceramic, a composite piezoelectric material, and a crystalline material.

In one embodiment, the fixing module is a ring shaped structure.

In one embodiment, the fixing module is made of an organic glass material or a plastic.

The advantages of the present embodiment are as follows. In the conscious animal ultrasonic neural regulation device of the conscious animal of the present disclosure, the single array element piezoelectric ceramic adopts the high power piezoelectric material, and the matched ultrasonic electronic system is supplemented, to perform the accurate ultrasonic stimulation on the cerebral cortex and subcortex of the animal, thereby exploring and verifying the stimulation effect of the ultrasound on the animal, which is easy in operation and convenient in use.

DETAILED DESCRIPTION

In the following description, numerous specific details are set forth to provide a thorough understanding of the present disclosure. The present disclosure may be implemented without some or all these specific details. In other instances, well known process operations would not be described in detail in order to not unnecessarily obscure the present disclosure. Even though hereinafter the present disclosure will be described in detail in conjunction with specific embodiments, it should be understood that it is not intended to limit the present disclosure to the embodiments.

Figure 1:
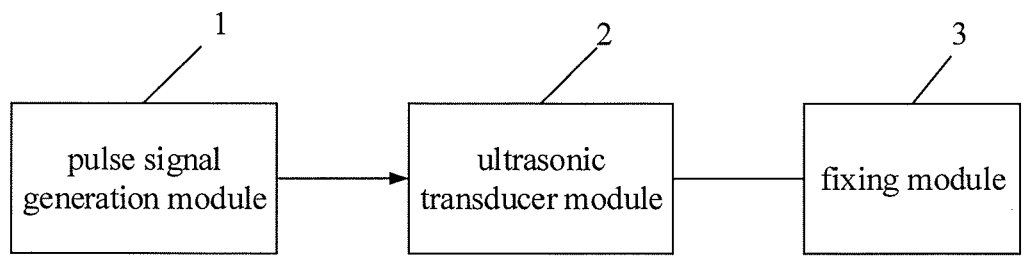
FIG. 1 is a structural schematic diagram illustrating a conscious animal ultrasonic neural regulation device according to the present disclosure.

Provided is a conscious animal ultrasonic neural regulation device, as shown in FIG. 1, specifically including a pulse signal generation module 1, a transducer module 2 and a fixing module 3.

Figure 2:
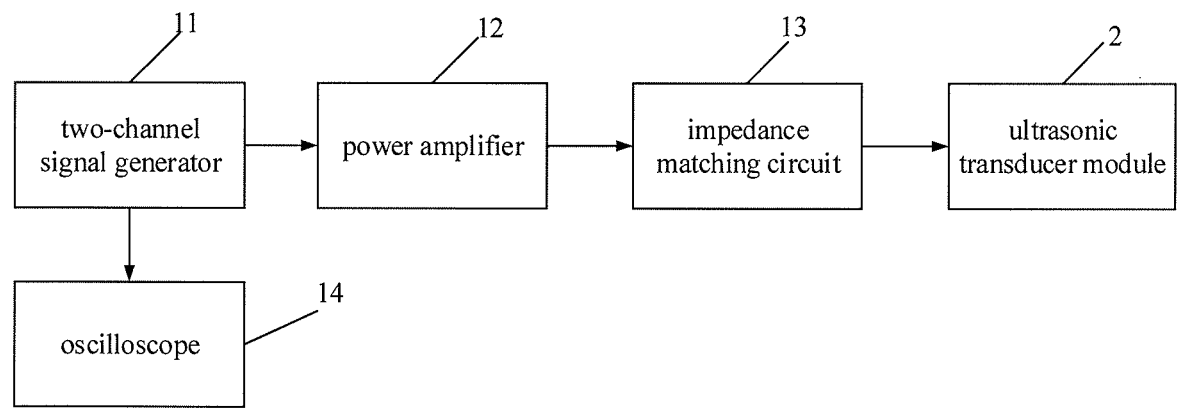
FIG. 2 is a structural schematic diagram illustrating a pulse signal generation module of a conscious animal ultrasonic neural regulation device according to the present disclosure.

The above modules and connection relationships thereof are specifically described below. The pulse signal generation module 1 is configured to generate a pulse signal with high energy. As shown in FIG. 2, the pulse signal generation module 1 includes an independent two-channel signal generator 11 configured to generate a neural regulation pulse waveform; a power amplifier 12 connected with the independent two-channel signal generator 11 and configured to increase an energy of the regulation pulse waveform; and an impedance matching circuit 13 connected with the power amplifier 12 and configured to perform personalization design based on an actual measured impedance value of a piezoelectric array element to realize the impedance matching. The pulse signal generation module 1 further includes an oscilloscope 14 connected with the independent two-channel signal generator 11 and configured to observe an output waveform.

Figure 3:
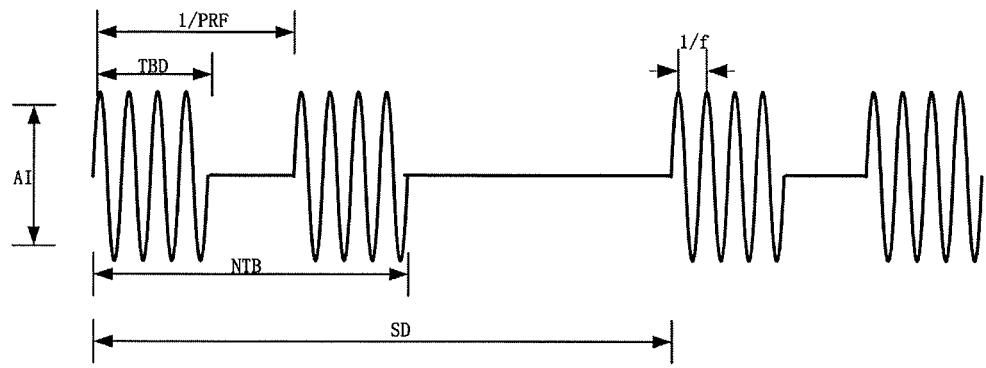
FIG. 3 is an oscillogram illustrating an ultrasonic neural regulation pulse generated by a pulse signal generation module.

The two-channel signal generator 11 is configured to generate the ultrasonic neural regulation pulse waveform, as shown in FIG. 3. A channel 1 in the two channels is configured to control a pulse repetition frequency PRF, a number of pulses NTB, and a pulse period SD, while a channel 2 is configured to control a fundamental frequency f, a number of fundamentals TBD and an output voltage AI. The channel 2 may choose the external trigging as the trigging manner, and the external triggering source thereof is the TTL signal of the channel 2. The signal of the channel 2 is connected to the oscilloscope 14 and the power amplifier 12 respectively through a three-way BNC wire. The oscilloscope 14 is configured to observe the output waveform. The power amplifier 12 is configured to increase the energy of the waveform output by the signal generator.

The impedance matching circuit 13 is configured to perform corresponding design based on the actual measured impedance value of the prepared piezoelectric array element, to ensure that the power amplifier 12 and the piezoelectric array element 23 can realize 50-ohm impedance matching, and realize that the energy of the power amplifier 12 can enter into the transducer module 2 without attenuation.

In the present disclosure, the two-channel signal generator 11 has the fundamental frequency at least in a range of 0.1 MHz to 5 MHz, may independently generate a sinusoidal signal and a square wave signal, and has a TTL gate trigger output function. In operation, the practicability of the present disclosure can be further enhanced by adopting different pulse repetition frequencies, different pulse durations, different fundamental frequencies, different numbers of fundamentals and different numbers of the pulses according to the stimulation site and the stimulation effect. The power amplifier 12 has a frequency band in a range of 0.1 MHz to 5 MHz, and a power range of 50 W to 150 W.

The structures and functions of the ultrasonic transducer module 2 and the fixing module 3 are described in detail below based on FIG. 4.

The ultrasonic transducer module 2 is configured to convert the pulse signal generated by the pulse signal generation module 1 into the ultrasound. As shown in FIG. 4, the transducer module 2 includes a leading wire 20, a piezoelectric array element 23 and a backing 21. The piezoelectric array element 23 is connected to the leading wire 20. In one embodiment, the leading wire 20 may be welded on the piezoelectric array element 23, and then connected to the impedance matching circuit 13. In another embodiment, the piezoelectric array element 23 is connected to a cable (not shown in the drawings) through the leading wire 20. The cable is connected to the impedance matching circuit 13 and configured to receive the electrical signal generated by the pulse signal generation module 1. In one embodiment, the cable is selected to be 50 ohm.

In one embodiment, the piezoelectric array element 23 is composed of a single array element, has an arc shaped structure capable of reaching the neural regulation depth, and is configured to focus the ultrasound generated by the piezoelectric array element on the target point of the animal brain region. Namely, the arc surface of the single array element transducer has the following feature: a focal point caused by the curvature of transducer can overlap the brain target region in focus axial length and longitudinal length. In addition, the realizable focus depth of the piezoelectric array element 23 provided by the present embodiment is preferably 3-to-4 mm greater than the functioning target region, so that the stimulation device prepared is small in size, light in weight, and easy to fixed in the animal brain. In the present disclosure, the piezoelectric material of the piezoelectric array element includes a piezoelectric ceramic, a composite piezoelectric material, and a crystalline material. In another embodiment, in operation, the practicability of the neural regulation device of the present disclosure can be further enhanced by choosing different areas and materials of piezoelectric materials based on the size of the brain stimulation region.

The epoxy resin is chosen for the material of the backing 21, which is poured into the upper fixing module 26 in a liquid state, and then solidified to protect the piezoelectric array element 23 and fix leading wire 20. The material of the backing 21 further needs to reserve a water inlet 25 and an air outlet 27 for injecting the deionized water. The deionized water is injected into the water inlet 25. The water inlet 25 and the air outlet 27 are sealed by a sealing film after no air bubble is observed in the fixing module 3. In the present disclosure, the deionized water is used in place of the ultrasonic coupling agent, which ensures that the ultrasound can enter into the brain target region from the piezoelectric array element 23 without attenuation.

Figure 4:
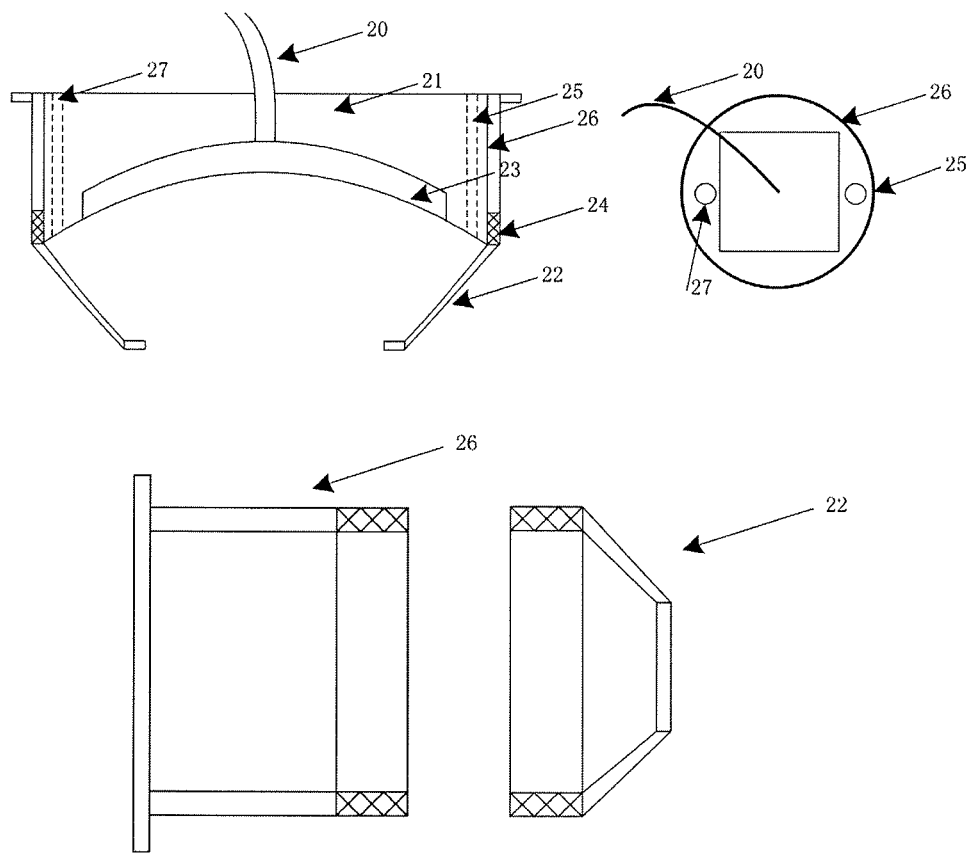
FIG. 4 is an assembling structural schematic diagram illustrating a transducer module and a fixing device module of a conscious animal ultrasonic neural regulation device according to the present disclosure.

As shown in FIG. 4, the fixing module 3 includes an upper fixing module 26 and a lower fixing module 22. The upper fixing module 26 is configured to fix the ultrasonic transducer module 2. The lower fixing module 22 is configured to be fixed on the animal neural regulation target point (animal brain) through the dental cement and skull nail. In one embodiment, an ultrasonic emission path in the ultrasonic neural regulation is determined, the lower fixing module 22 is fixed on the skull surface through which the emission path passes, and the upper fixing module 26 is screwed by the screw 24 (connecting component), so that the piezoelectric array element 23 is fixed on the animal brain. In one embodiment of the present disclosure, the upper fixing module 26 and the lower fixing module 22 adopt a circular ring and a conical cone structure, and plastic or organic glass material. The ultrasonic transducer system is fixed by the upper circular ring, while the lower conical cone is fixed on the animal neural regulation target point.

The fixing module 3 of the present disclosure can be designed in different sizes based on the area of the transducer module 2 and the size of the skull of the experimental animal, to satisfy the neural regulation of the different brain area. In addition, the fixing module 2 of the present disclosure is small in volume and light in weight, and can realize that the animal is equipped with the ultrasonic regulation device in a conscious and free moving state, and realize that the ultrasonic neural regulation function is evaluated in a no-anesthetic state. In addition, the conscious animal ultrasonic neural regulation device can be used for the free moving animal (such as rat), convenient for the animal (rat) to be equipped for a long time, and the treatment of the ultrasound on the brain diseases to be studied, thereby providing preliminary clinical support.

What is claimed is:

1. A conscious animal ultrasonic neural regulation device, comprising a pulse signal generation component, an ultrasonic transducer component and a fixing component;
   wherein the pulse signal generation component is configured to generate a pulse signal;
   the ultrasonic transducer component is configured to convert the pulse signal into an ultrasound;
   the fixing component comprises an upper fixing component and a lower fixing component;
   wherein the upper fixing component is configured to fix the ultrasonic transducer component, and the lower fixing component is configured to be fixed on an animal neural regulation target point;
   the upper fixing component and the lower fixing component are connected by a connecting component,
   wherein the pulse signal generation component comprises:
   an independent two-channel signal generator, configured to generate a pulse waveform for neural regulation;
   a power amplifier, configured to increase an energy of the regulation pulse waveform; and
   an impedance matching circuit, configured to perform personalization design based on an actual measured impedance value of a piezoelectric array element, to realize impedance matching;
   wherein the two-channel signal generator comprises a first channel and a second channel, the first channel is configured to control a pulse repetition frequency, a number of pulses, and a pulse period, the second channel is configured to control a fundamental frequency, a number of fundamentals and an output voltage, a trigging manner of the second channel is external trigging via Transistor-Transistor Logic (TTL) signal of the second channel; and
   wherein the ultrasonic transducer component comprises a leading wire, the piezoelectric array element and a backing;
   the piezoelectric array element is connected to the leading wire, and the leading wire is connected to the impedance matching circuit of the pulse signal generation component;
   the backing is made of an epoxy resin material, and provided with a water inlet and an air outlet, the water inlet and the air outlet are configured to inject deionized water into the backing;
   wherein the piezoelectric array element is composed of a single array element, the single array element has an arc shaped structure capable of reaching a neutral regulation depth, and the piezoelectric array element is configured to focus the ultrasound generated by the piezoelectric array element on an animal brain target region through the deionized water injected into the backing.

2. The device according to claim 1, wherein the pulse signal generation component further comprises an oscilloscope connected with the independent two-channel signal generator and configured to observe an output waveform.

3. The device according to claim 1, wherein the two-channel signal generator has a fundamental frequency at least in a range of 0.1 MHz to 5 MHz, is configured to independently generate a sinusoidal signal and a square wave signal, and has a TTL gate trigger output function.

4. The device according to claim 1, wherein the power amplifier has a frequency band in a range of 0.1 MHz to 5 MHz, and a power range of 50 W to 150 W.

5. The device according to claim 1, wherein a piezoelectric material of the piezoelectric array element comprises at least one of a piezoelectric ceramic, a composite piezoelectric material, and a crystalline material.

6. The device according to claim 1, wherein the fixing component is a ring shaped structure.

7. The device according to claim 1, wherein the fixing component is made of an organic glass material or a plastic.

* * * * *